(12) United States Patent
Roper et al.

(10) Patent No.: US 9,958,362 B1
(45) Date of Patent: May 1, 2018

(54) MICROSCOPE SAMPLE PREPARATION DEVICE

(71) Applicant: The Florida State University Research Foundation, Inc., Tallahassee, FL (US)

(72) Inventors: Michael G. Roper, Tallahassee, FL (US); Nikita Mukhitov, Tallahassee, FL (US); Scott Stagg, Tallahassee, FL (US); John Spear, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 65 days.

(21) Appl. No.: 15/263,949

(22) Filed: Sep. 13, 2016

Related U.S. Application Data

(60) Provisional application No. 62/236,368, filed on Oct. 2, 2015.

(51) Int. Cl.
*G01N 1/30* (2006.01)
*G01N 1/31* (2006.01)
*H01J 37/20* (2006.01)

(52) U.S. Cl.
CPC ............... *G01N 1/312* (2013.01); *G01N 1/30* (2013.01); *H01J 37/20* (2013.01); *H01J 2237/2002* (2013.01); *H01J 2237/2602* (2013.01)

(58) Field of Classification Search
CPC ........................................................ G01N 1/30
USPC .................... 422/502–503; 436/174, 180
See application file for complete search history.

(56) References Cited

U.S. PATENT DOCUMENTS

| | | | |
|---|---|---|---|
| 6,743,632 B2 | 6/2004 | Clarke et al. | |
| 2002/0187074 A1 | 12/2002 | O'Connor et al. | |
| 2008/0250881 A1* | 10/2008 | Dona | H01J 37/20 73/864.91 |
| 2008/0258056 A1* | 10/2008 | Zaykova-Feldman | G01N 23/04 250/307 |
| 2009/0311717 A1* | 12/2009 | De Sonneville | B01L 3/502715 435/7.2 |

(Continued)

OTHER PUBLICATIONS

Auroux et al., Miniaturised nucleic acid analysis, Lab Chip, 2004, vol. 4, pp. 534-546.

(Continued)

*Primary Examiner* — Arlen Soderquist
(74) *Attorney, Agent, or Firm* — Nicholas Pfeifer; Smith & Hopen, P.A.

(57) ABSTRACT

A sample preparation device for electron microscopy (EM) that is configured to eliminate user-to-user variations and environment contaminations, which are often present in the conventional method of sample preparation. The device not only provides a means for evenly and reproducibly delivering a fluid or sample to an EM grid, but also provides a means for sealing the EM grid in an air-tight chamber and delivering air-sensitive samples to the EM grid. The platform may comprise readily fabricated glass chips with features integrated to preserve the integrity of the sample grid and to facilitate its extraction. The methods may eliminate the element of user dependent variability and thus improve the throughput, reproducibility and translation of these methods.

17 Claims, 16 Drawing Sheets

(56) References Cited

U.S. PATENT DOCUMENTS

| | | | | |
|---|---|---|---|---|
| 2010/0269572 | A1* | 10/2010 | Jiang | G01N 21/0303 73/61.41 |
| 2011/0238225 | A1 | 9/2011 | Tripathi et al. | |
| 2012/0177543 | A1 | 7/2012 | Battrell et al. | |
| 2012/0241607 | A1* | 9/2012 | Bose | H01J 37/20 250/307 |
| 2015/0273470 | A1* | 10/2015 | Hoffmann | B01L 3/502753 435/34 |
| 2015/0283514 | A1* | 10/2015 | Aguilar | G01N 15/12 204/540 |

OTHER PUBLICATIONS

Callaway, The Revolution Will Not Be Crystallized, Move Over X-Ray Crystallography. Cryo-Electron Microscopy Is Kicking Up a Storm in Structural Biology by Revealing the Hidden Machinery of the Cell., Nature 2015, vol. 525, pp. 172-174.

Cao et al., Microfluidic multi-analyte gradient generator, Anal Bioanal Chem, 2010 vol. 398, pp. 1985-1991.

Castro-Hartmann et al., The ArrayGrid: A methodology for applying multiple samples to a single TEM specimen grid, Ultramicroscopy 2013, vol. 135, pp. 105-112.

Cho et al., How the capillary burst microvalve works, J. of Colloid and Interface Science 2007, vol. 306, pp. 379-385.

De Carlo et al., Negative staining and cryo-negative staining of macromolecules and viruses for TEM, Micron 2011, vol. 42, pp. 117-131.

Dertinger et al., Generation of Gradients Having Complex Shapes Using Microfluidic Networks, Anal. Chem. 2001, vol. 73, pp. 1240-1246.

Dhumpa et al., Negative Feedback Synchronizes Islets of Langerhans, Biophysical Journal 2014, vol. 106, pp. 2275-2282.

Dhumpa et al., Measurement of the entrainment window of islets of Langerhans by microfluidic delivery of a chirped glucose waveform, Integr. Biol., 2015, vol. 7, pp. 1061-1067.

Easley et al., A fully integrated microfluidic genetic analysis system with sample-in-answer-out capability, PNAS, 2006, vol. 103, No. 51, pp. 19272-19277.

Gabler et al., Studies of Ribosomal Diffusion Coefficients Using Laser Light-Scattering Spectroscopy, Biophysical Journal, vol. 14, 1974, pp. 528-544.

Giss et al., Exploring the interactome: microfluidic isolation of proteins and interacting partners for quantitative analysis by electron microscopy. Anal. Chem. 2014, vol. 86, pp. 4680-4687.

Hong et al., A novel in-plane passive microfluidic mixer with modified Tesla structures, Lab Chip, 2004, vol. 4, pp. 109-113.

Jain et al., Spotiton: A prototype for an integrated inkjet dispense and vitrification system for cryo-TEM, Journal of Structural Biology, 2012, vol. 179, pp. 68-75.

Kemmerling et al., Connecting mu-fluidics to electron microscopy, Journal of Structural Biology 2012, vol. 177, pp. 128-134.

Kemerling et al., Single-cell lysis for visual analysis by electron microscopy, J. Struct. Biol. 2013, vol. 183, pp. 467-473.

Kirby et al., Digital Microfluidics: An Emerging Sample Preparation Platform for Mass Spectrometry, Anal. Chem. 2013, vol. 85, pp. 6178-6184.

Li et al., Integration of Isoelectric Focusing with Parallel Sodium Dodecyl Sulfate Gel Electrophoresis for Multidimensional Protein Separations in a Plastic Microfludic Network, Anal. Chem. 2004, vol. 76, pp. 742-748.

Lu et al., Monolithic microfluidic mixing-spraying devices for time-resolved cryo-electron microscopy, Journal of Structural Biology, 2009, vol. 168, pp. 388-395.

Lu et al., Gas-assisted annular microsprayer for sample preparation for time-resolved cryo-electron microscopy, J. Micromech. Microeng. 2014, vol. 24, No. 115001, pp. 1-9.

Magliery et al., Protein stability by number: high-throughput and statistical approaches to one of protein science's most difficult problems, Current Opinion in Chemical Biology 2011, vol. 15, pp. 443-451.

Mukhitov et al., Optimization of a microfluidic electrophoretic immunoassay using aPeltier cooler, Journal of Chromatography A 2014, vol. 1367, pp. 154-160.

Mukhitov et al., Interfacing Microfluidics with Negative Stain Transmission Electron Microscopy, Anal. Chem. 2016, vol. 88, pp. 629-634.

Noble et al., A pseudoatomic model of the COPII cage obtained from cryo-electron microscopy and mass spectrometry, Nature structural & molecular biology, 2013, vol. 20, No. 2, pp. 167-174.

Ohi et al., Negative Staining and Image Classification—Powerful Tools in Modern Electron Microscopy, Biol. Proced. Online 2004, vol. 6, No. 1, pp. 23-34.

Rames et al., Optimized Negative Staining: a High-throughput Protocol for Examining Small and Asymmetric Protein Structure by Electron Microscopy, Electron Microscopy. J. Vis. Exp. 2014, vol. 90, e51087, pp. 1-15.

Sasaki et al., Fluid mixing using AC electrothermal flow on meandering electrodes in a microchannel, Electrophoresis 2012, vol. 33, pp. 2668-2673.

Schrell et al., Frequency-encoded laser-induced fluorescence for multiplexed detection in infrared-mediated quantitative PCR, Analyst, 2014, vol. 139, pp. 2695-2701.

Squires et al., Microfluidics: fluid physics at the nanoliter scale, Reviews of Modem Physics 2005, vol. 77, pp. 977-1026.

Stagg et al., Structure of the Sec13/31 COPII coat cage, Nature 2006, vol. 439, pp. 234-238.

Stagg et al., Structural Basis for Cargo Regulation of COPII Coat Assembly, Cell 2008, vol. 134, pp. 474-484.

Zhang et al., Microfluidic System for Generation of Sinusoidal Glucose Waveforms for Entrainment of Islets of Langerhans, Anal. Chem. 2010, vol. 82, pp. 6704-6711.

Zhao et al., Surface-directed liquid flow inside microchannels. Science 2001, vol. 291, pp. 1023-1026.

* cited by examiner

MICROSCOPE SAMPLE PREPARATION DEVICE

CROSS-REFERENCE TO RELATED APPLICATIONS

This non-provisional application is a continuation of and claims priority to provisional application No. 62/236,368, entitled "ELECTRON MICROSCOPE SAMPLE PREPARATION DEVICE," filed Oct. 2, 2015 by the same inventors.

BACKGROUND OF THE INVENTION

1. Field of the Invention

This invention relates, generally, to the field of microscopy. More specifically, it relates to preparation of samples for electron microscopy.

2. Brief Description of the Prior Art

Preparation of high quality samples is critical for structure determination of biomolecules. Sample preparation for negative stain EM is typically done by hand and consists of a series of blotting steps of both the sample and heavy metal stain. The stain is used to introduce contrast to the images and to lock the native structure of the protein into place.

Conventional negative staining of samples on EM grids is the primary method used by most EM labs to evaluate their samples and can be the only method for specimen preparation of small or highly heterogeneous samples. There are almost as many protocols for making negative stain grids as there are EM labs, and researchers adhere to their own protocols that have been developed for years. For example, one protocol, as depicted in FIG. 1, might call for retrieving EM grid 102 using tweezers 104, hand pipetting microliter sample 103 onto the carbon-coated copper grid 102, hand blotting sample 103 with absorbent filter paper 106 to remove most of the liquid, hand pipetting a microliter volume of heavy metal stain 105 onto EM grid 102, and again hand blotting EM grid 102 with absorbent paper 106 to remove excess stain. Alternately, other labs advocate transferring a grid between different drops of sample, water, and stain and then blotting.

There are several disadvantages to the conventional method of preparing an EM sample by hand. First, the grid and sample are open to the environment, and thus, subject to unwanted contamination. Second, the sample is exposed to air, which prevents the use of air-sensitive samples. Third, there is a large amount of variability within a single EM grid, between grids stained by a single user, and even more variability between users.

The significance of the variability is so great that the preparation is frequently compared to an art-form. Typically, this problem is overcome by arbitrarily sampling regions of the grid until one can be found where the specimen subjectively looks the best. However, this irreproducibility can lead to bias, staining artifacts, and poor signal-to-noise, which can degrade image resolution and information content.

A few examples of microfluidic systems have been published for sample preparation of cryo-EM samples or for negative-stained samples (Jain et al., 2012; Kemmerling et al., 2012; Lu et al., 2009; Lu et al., 2014). However, these were highly specialized devices which would need to be redesigned for specific samples. Additionally, the designs relied on sample spraying techniques that can be disruptive to the structure of macromolecular complexes. Proteins are often prone to denaturation at the air/water interface, and spraying techniques are limited to samples that are relatively insensitive to the interface, such as well-behaved samples like ribosomes and GroEL. Ultimately, these protocols offered no quantitative assessment of the sample. Id.

Collectively the technologies mentioned above may have some merit to improve throughput and reproducibility of sample preparation, but they required the utilization of robotics thus hindering the methods' translation. Moreover, these advances are auxiliary additions to the same preparation workflow.

Accordingly, what is needed is a device and method for preparing a microscope sample that remove or minimize user variation and prevent exposure of the sample to air. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a device and method for preparing an EM sample that remove or minimize user variation and prevent exposure of the sample to air is now met by a new, useful, and nonobvious invention.

The present disclosure is directed to a microfluidic sample preparation device, preferably for electron microscopy. Various embodiments may allow for sealing of an EM grid, facile and reproducible delivery of sample, followed by delivery of subsequent solutions that may be negative stains or other biological samples. According to various embodiments, the EM grid may be contained in a grid chamber using a plurality of support barriers and may be gently and easily removed with an extraction divot disposed at least partially below the grid chamber. The fluid may be directed to the grid using channels integrated into the platforms of the microfluidic system. Single or multiple grids may be housed in a platform, which may allow for high throughput testing. For example, a device with nine grids may require less than 1 µL of sample per grid. This may allow more screening in circumstances where sample quantity is limited.

Various embodiments comprise a device to deliver air-sensitive samples to an EM grid via an air tight chamber. This technology fills a niche for which no similar technology currently exists. Traditionally, EM staining is a tedious and time consuming task that offers little reproducibility. The conventional staining method is done in a manual fashion in an open environment, which may introduce contamination, is not viable for air-sensitive samples, and may be plagued by user-to-user variations.

Various embodiments may comprise two platforms, which may be comprised of etched pieces of glass, aligned to one another forming an internal chamber sized to house the EM grid. Integrated microfluidic channels allow the sample to be delivered to the grid in an automated fashion. Timing may be introduced using automated or integrated valves allowing time-dependent snapshots of the sample.

The long-standing but heretofore unfulfilled need for an EM sample preparation device capable of sealing of an EM grid from exposure to air, facile and reproducible delivery of sample, followed by delivery of subsequent solutions that may be negative stains or other biological samples, and methods for its use, are now met by a new, useful, and nonobvious invention.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention includes a novel device and method for preparing a sample for EM imaging. The present invention provides an innovative approach to 1) create a robust and reproducible method for negative staining of EM grids; 2) automate preparation of multiple samples simultaneously; and 3) integrate quantitative assessments of sample stability. The technologies described herein are suitable for applications across the field of EM and will have a significant impact on a multitude of other biological systems.

Figure 2:
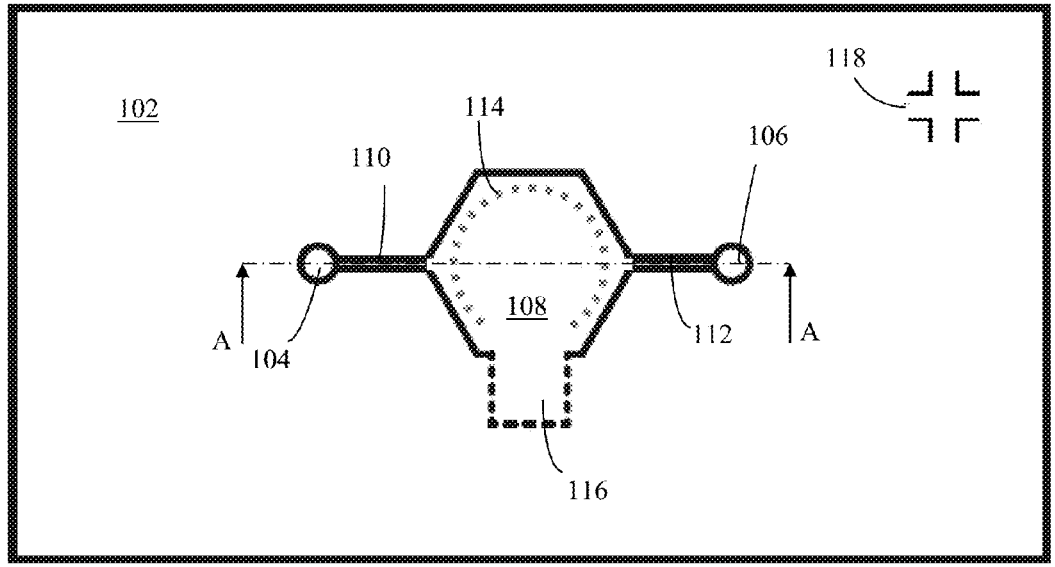
FIG. 2 is an overhead view of an embodiment of a bottom platform.

As shown in FIG. 2, an embodiment of the novel apparatus includes bottom platform 102 having inlet 104, outlet 106, and grid chamber 108 disposed between inlet 104 and outlet 106. Grid chamber 108 is in fluid communication with inlet 104 and outlet 106 through inlet channel 110 and outlet channel 112, respectively. Bottom platform 102 further includes a plurality of grid support barriers 114 disposed in grid chamber 108 and extraction divot 116 located at least partially within the outer perimeter of grid chamber 108. Bottom platform 102 also preferably includes at least one alignment marker 118.

Bottom platform 102 is preferably flat and may be comprised of generally any material including, but not limited to glass, metals, ceramics, plastics, silicon, and elastomers. Fabrication may be achieved through known processes for creating microfluidic devices including, but not limited to lithography, 3D printing, hot embossing, and milling. The fabrication method is at least partially dependent on the structural features of the bottom platform and the material included in the bottom platform.

Figure 3:
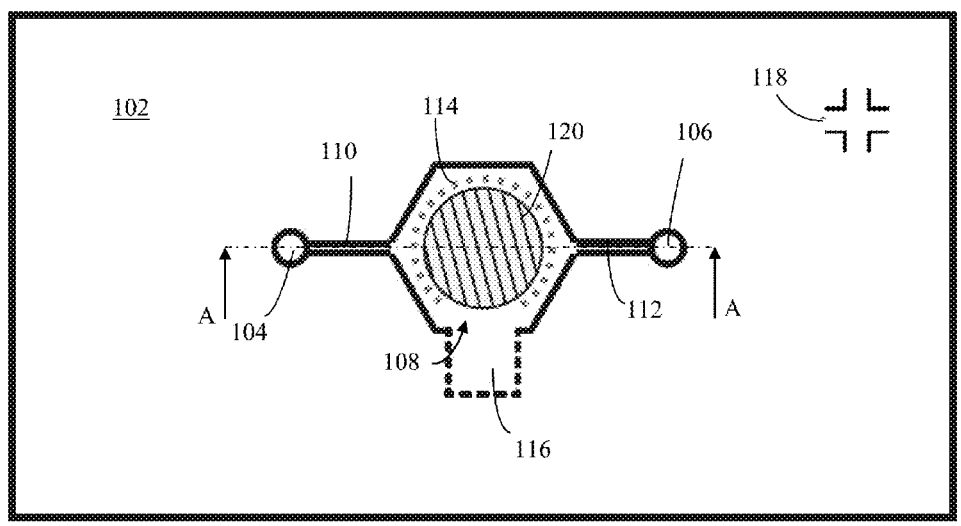
FIG. 3 is an overhead view of the embodiment provided in FIG. 2 with the addition of a microscope grid.

As depicted in FIG. 3, EM grid 120 is intended to rest in grid chamber 108 within the perimeter created by support barriers 114. The exemplary embodiment shows grid chamber 108 as hexagonal in shape, but any shape is contemplated. Support barriers 114 are strategically arranged to create a perimeter of a proper size for receiving and securing EM grid 120 within grid chamber 108. The support barriers 114 minimize grid movement while a pressure-driven fluid flow passes through grid chamber 108. The fragile nature of EM grid 120 and its carbon coating require that EM grid 120 remain generally static as the pressurized flow overtakes EM grid 120. It was discovered that the absence of support barriers 114 resulted in EM grid 120 sliding around grid chamber 108 upon application of fluid, thus causing the carbon film to tear.

In the depicted embodiment, support barriers 114 are arranged in a generally circular fashion. The overall pattern/arrangement of barriers 114 is dependent on the shape of EM grid 120, and thus, may be arranged in a different pattern to secure EM grid 120 within grid chamber 108.

In an embodiment, the arrangement of barriers 114 must include a gap between barriers 114 sufficiently sized to account for extraction divot 116 disposed within the gap. Extraction divot 116 allows for easy removal of the fragile EM grid 120 using sharp-tipped forceps or a similarly designed device. Extraction divot 116 further aids in preventing EM grid 120 from sticking to bottom platform 102 when a user attempts to remove EM grid 120 from grid chamber 108.

Figure 1:
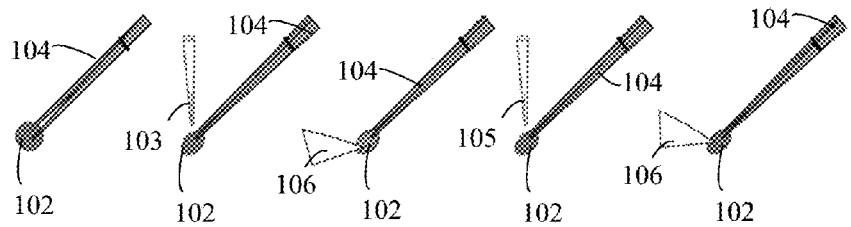
FIG. 1 depicts the conventional method of preparing a sample for EM imaging highlighting the degree of manual interaction required to complete the preparation.
Figure 4:
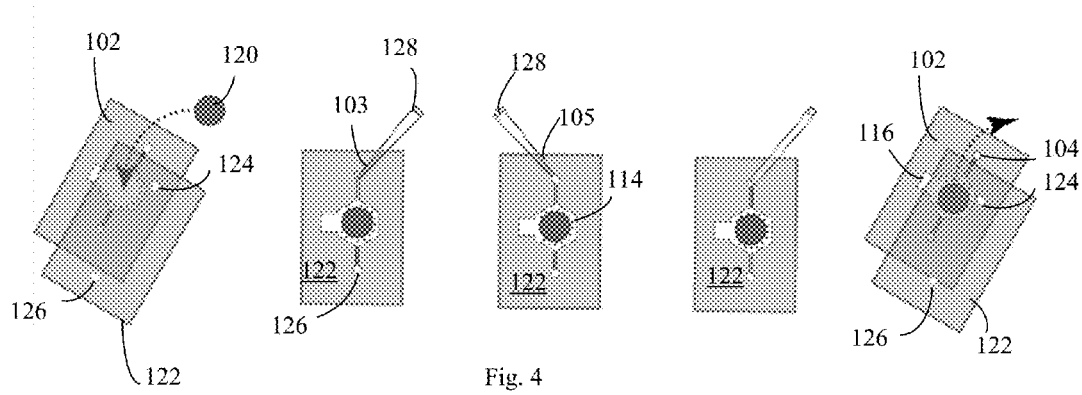
FIG. 4 is an embodiment of the novel method of preparing an EM sample.

Referring now to FIG. 4, bottom platform 102 is designed to receive top platform 122. In its simplest form, top platform 122 is a simple barrier secured in overlying relation to bottom platform 102. Top platform 122 includes inlet aperture 124 and outlet aperture 126 to provide a fluid passage to the inlet 104 and outlet 106, respectively. Upon loading EM grid 120 into chamber 108, all the externally conducted steps shown in FIG. 1 can be performed in a temporarily sealed environment minimizing the exposure and the variability resulting from manual EM grid handling. EM grid 120 is preferably sealed into chamber 108 using bottom platform 102 and top platform 122 to ensure accurate and reproducible flow patterns for sample preparation An embodiment of the novel method of EM sample preparation, using an embodiment of the novel device, is illustrated in FIG. 4. The sample is prepared according to the five general steps executed from left to right. In the first step, EM grid 120 is deposited within support barriers 114 located in grid chamber 108 in bottom platform 102. Top platform 122 is secured in overlying relation to bottom platform 102 with inlet and outlet apertures 124, 126 respectively aligned with inlet 104 and outlet 106. In the second step, sample 103 is inserted into the system through inlet 124 using a fluid application device, such as pipette 128. The third step includes inserting stain 105 into the system using a fluid application device, such as pipette 128. The fourth step comprises drying the system using a gas inserted into aperture 124. Once EM grid 120 is adequately dried, top platform 122 is removed. EM grid 120 is removed from bottom platform 102 in the final step. Through the use of the microfluidic platforms, all the preparation steps are integrated into a single system overcoming the irreproducibility obstacles prevalent in EM sample preparation.

Figure 5A:
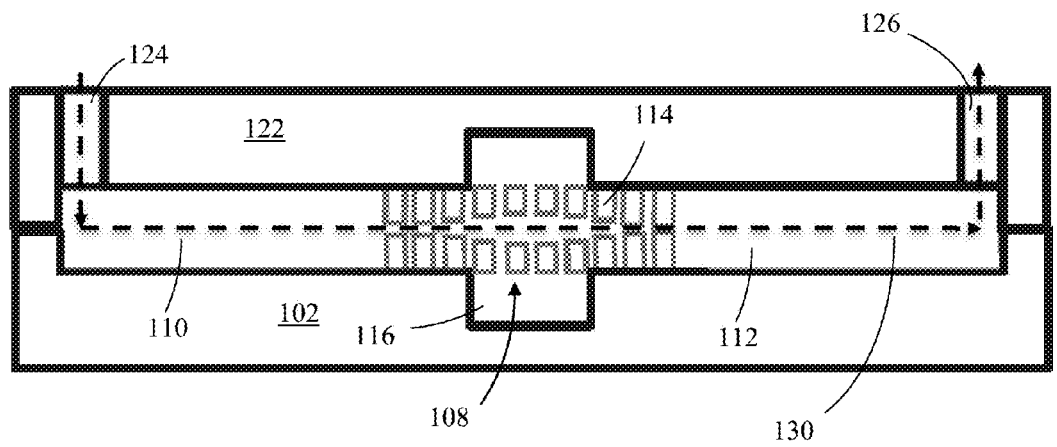
FIG. 5A is a section view of section line A-A in FIG. 2 with the inclusion of the top platform.
Figure 5B:
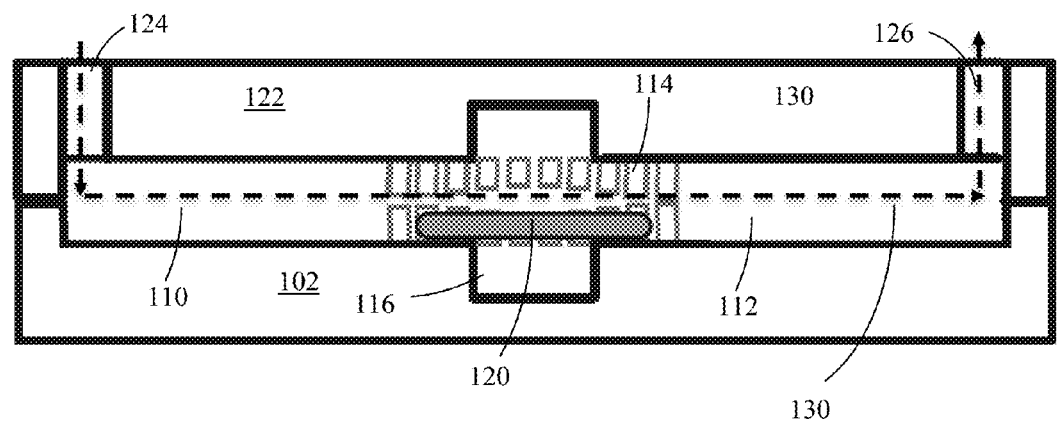
FIG. 5B is a section view of section line A-A in FIG. 3 with the inclusion of the top platform.

In experimental testing, EM grid 120 would often stick to the top platform 122 when top platform 122 was removed in step five above. The fragility of the EM grid 120 became an issue when attempting to remove EM grid 120 from top platform 122. As a result, a preferred embodiment of the present invention, as depicted in FIGS. 5A-5B, includes top platform 122 having etching in its lower surface that is similar to the etching in the upper surface of bottom plate 102. FIG. 5 provide a sectional view along section line A-A shown in FIGS. 2-3 and illustrates how fluid, depicted by arrows 130, passes into the system through inlet aperture 124 and then out of the system through outlet aperture 126. The figures depict inlet and outlet channels 110, 112 as having a depth generally equal to the depth of grid chamber 108, but the channels can be any size relative to the size of the grid chamber.

In an embodiment, the top platform is simply an inverted bottom platform to reduce manufacturing efforts. In yet another embodiment, top platform 122 simply includes an extraction divot disposed in the lower surface to allow a user to remove an EM grid stuck to the top platform using an extraction tool.

To ensure proper alignment of the top and bottom platforms 122, 102, an embodiment of the present invention may include each platform having an alignment marker 118 (See e.g. FIGS. 8-11 and 14). In an embodiment, the alignment marker on the top platform is designed to interact with the alignment marker on the bottom platform to prevent respective movement of the two platforms in the transversal and longitudinal directions. The alignment markers are disposed at least on the upper surface of the bottom platform and on the lower surface of the top platform.

As is discussed below in the experiment section, there was a substantial benefit from sealing the top and bottom platforms. Therefore, a preferred embodiment includes a sealed system to ensure accurate and reproducible flow patterns and also to protect the sample from the air-water interface. At the end of the sample preparation, however, the EM grid must be removed for visualization by EM. Therefore, a reversible sealing method for the system is required.

Figure 6A:
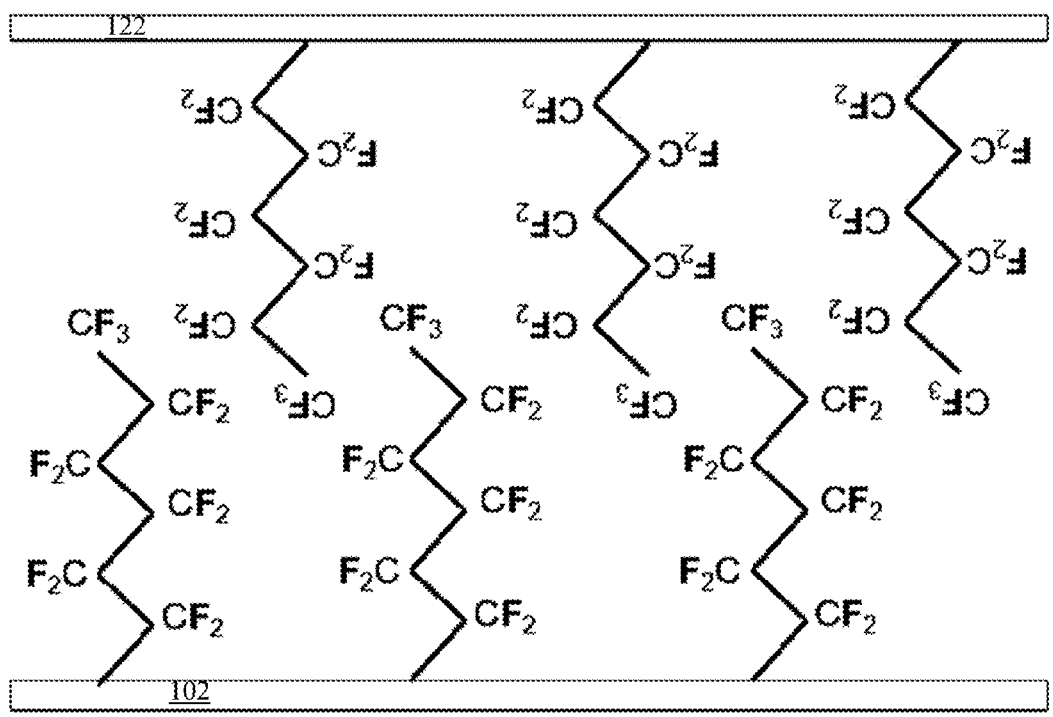
FIG. 6A depicts an example of functionalized top and bottom platforms using fluoropolymer.
Figure 6B:
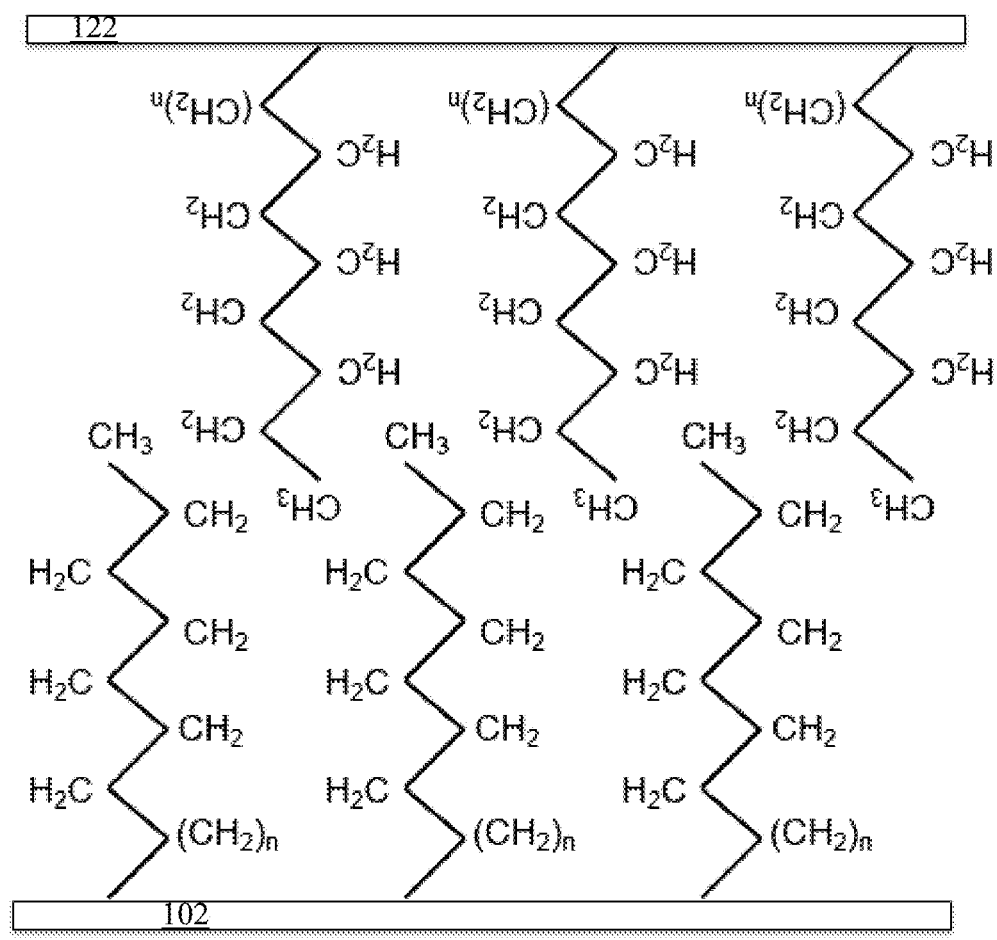
FIG. 6B depicts an example of functionalized top and bottom platforms using alkane chains.
Figure 6C:
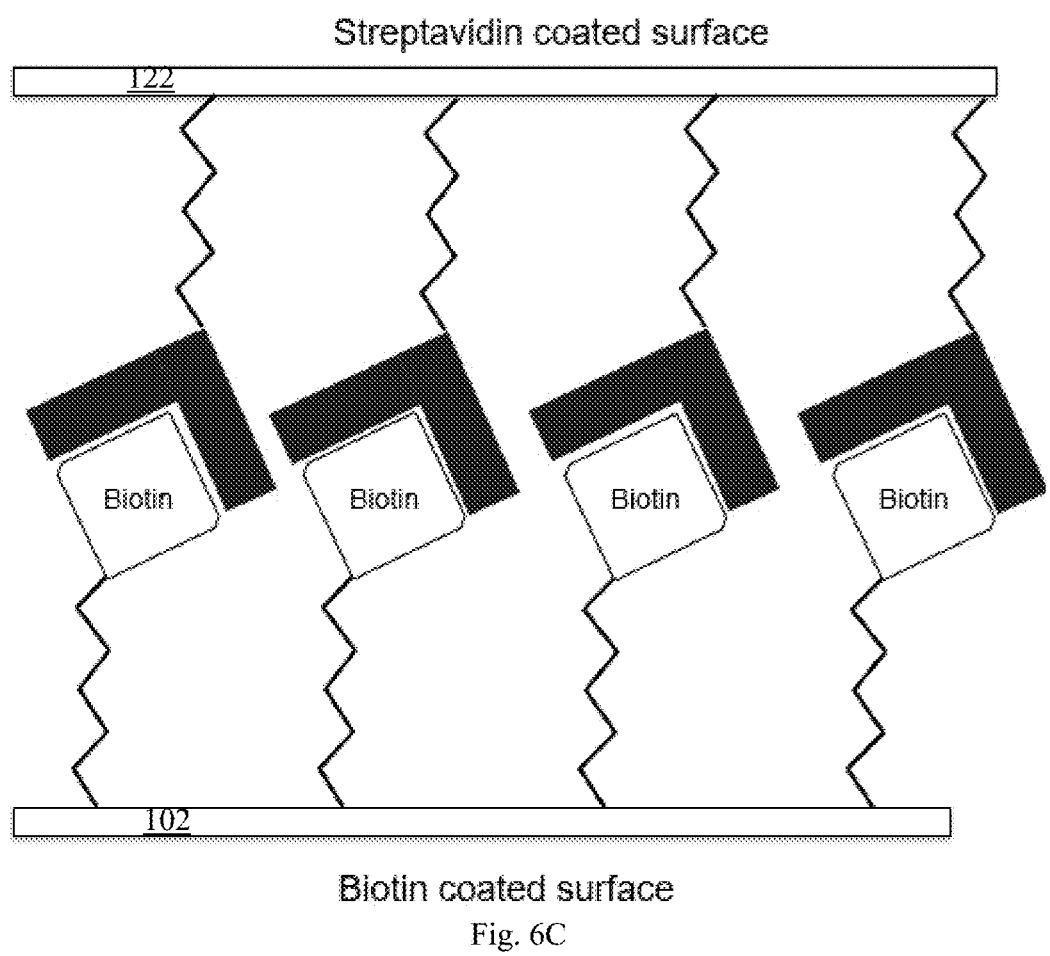
FIG. 6C depicts an example of functionalized top and bottom platforms using biotin-streptavidin reaction.

The system may employ functionalized materials for sealing the system. The different substrates can be functionalized in a panel of ways to provide different sample solvent/matrix compatibility. For example, functionalization methods include, but are not limited to fluorine functionalized surfaces (FIG. 6A), alkane functionalized surfaces (FIG. 6B), biotin-streptavidin (FIG. 6C), carbon coating by sputtering, plasma oxidized, and carbon coated and plasma oxidized. It should be noted that the plasma oxidation rendered the surface hydrophilic and led to rapid transfer of solution between slides. This strategy can be used to accelerate and guide the passage of fluid through the channels.

Alternatively, the bottom and top platforms may be temporarily sealed using mechanical devices, including, but not limited, to a binder clip, clamps, manifolds that have a built in screw/clamping system, magnets, or a device integrated into the top and bottom platforms. In an embodiment, a gasket is disposed between the sandwiched top and bottom platforms to seal the grid chamber and channels.

Figure 7:
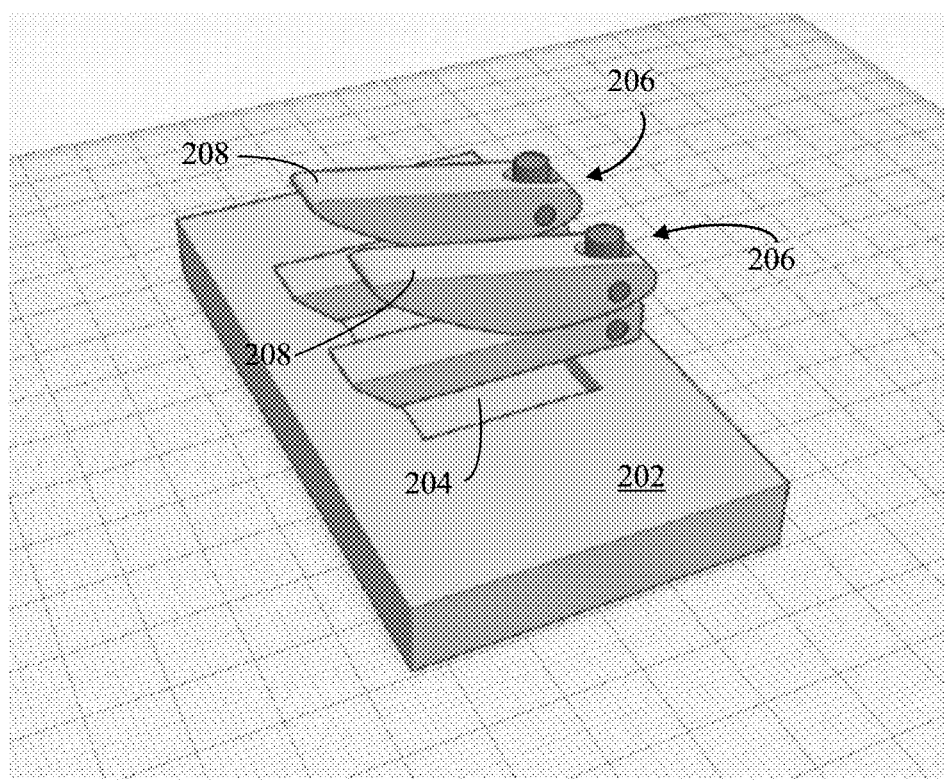
FIG. 7 is an exemplary embodiment of a mechanical clamp for securing the top and bottom platforms together.

A particular example of a mechanical clamping device is provided in FIG. 7. The device includes base platform 202 having recess 204 in which bottom and top platforms 102,122 (not shown) are intended to rest. Clamping arms 206 force platforms 102, 122 together when in the securing configuration shown. Clamping arms 206 may be opened by rotating the top assembly arm 208 in an outboard direction, which removes the clamping force on the platforms 102, 122. Bottom and top platforms 102,122 can then be easily removed from recess 204.

Fluid (sample, stain, rinse, etc.) delivery and control can take on various forms depending on the type of sample being prepared and the goals of the preparation. The method shown in FIG. 4 relies on pipette 128 for the delivery of the sample and stain to the grid chamber 108. Other manual fluid delivery options include, but are not limited to, a syringe pump, a surface tension/capillary action driven fluid, a vacuum at the outlet aperture 126, peristatic pumps, and tilting the system to rely on gravity to drive the fluid from inlet aperture 124 to outlet aperture 126. Many of these pressure-driven systems would be implemented "off-chip," but some could also be implemented directly within the microfluidic system using micro-fabrication techniques. Some of these micro-fabrication techniques require multiple layers of the device, which is compatible with this system.

Fluid delivery may, alternatively, be automated. These automated measure include, but are not limited to, "on-chip" valves or pumps, electroosmotic flow-voltage driven, and the use of a pre-filled tube having pre-measured segments of the sample, stain, rinse, etc.

In an embodiment, the fluid delivery mechanisms are coupled to the inlet aperture, and preferably also the outlet aperture, to maintain a sealed environment and ensure direct application into the system. The coupling can be achieved according to any method known by a person having ordinary skill in the art for securing a fluid delivery system to a microfluidic platform, including, but not limited to, press fitting tubes into the apertures, securing nano-port fitting in the apertures, and bonding a threaded reservoir into the apertures and then interfacing the reservoir with tubing and fittings.

The removal of manual handling and manual application of fluids during EM sample preparation, which is now possible with the present invention, opens the field of EM sample preparation to both high throughput production, microfluidic timers, and microfluidic gradient generators. It should be noted that the microfluidic features can be on the same device or a separate platform. A separate device having the microfluidic features is may be desirable for easily interchanging the preparation platforms.

Figure 8:
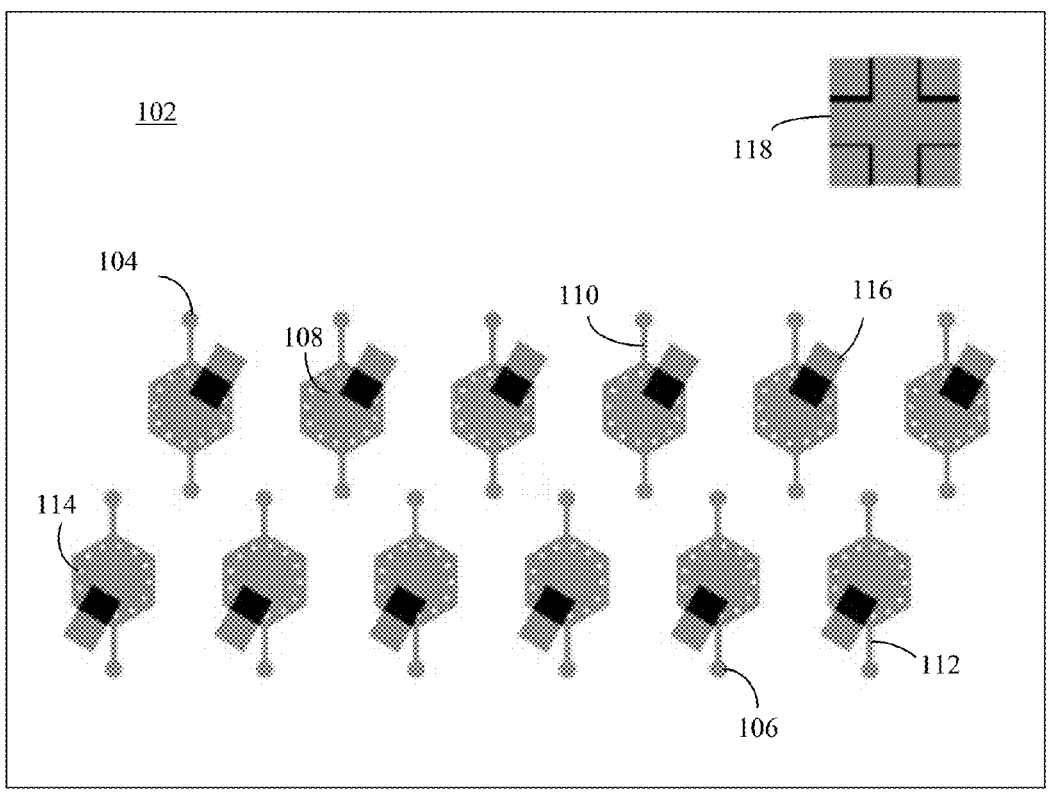
FIG. 8 is an embodiment of a bottom platform comprising multiple grid chambers.

Referring now to FIG. 8, an embodiment of the present invention provides a high throughput system for simultaneous preparation of multiple EM samples and multi-screening from the same sample. Bottom platform 102 includes twelve separate grid chambers 108 each with their own inlet 104 and outlet 106. Obviously alignment of bottom platform 102 and top platform (not shown) is critical when several grid chambers 108 are disposed in each platform. Thus, each platform includes alignment marker 118. Preferably alignment marker 118 on bottom platform 102 is designed to interconnect with an alignment marker on the top platform to prevent lateral and longitudinal movement between the two platforms.

Figure 9:
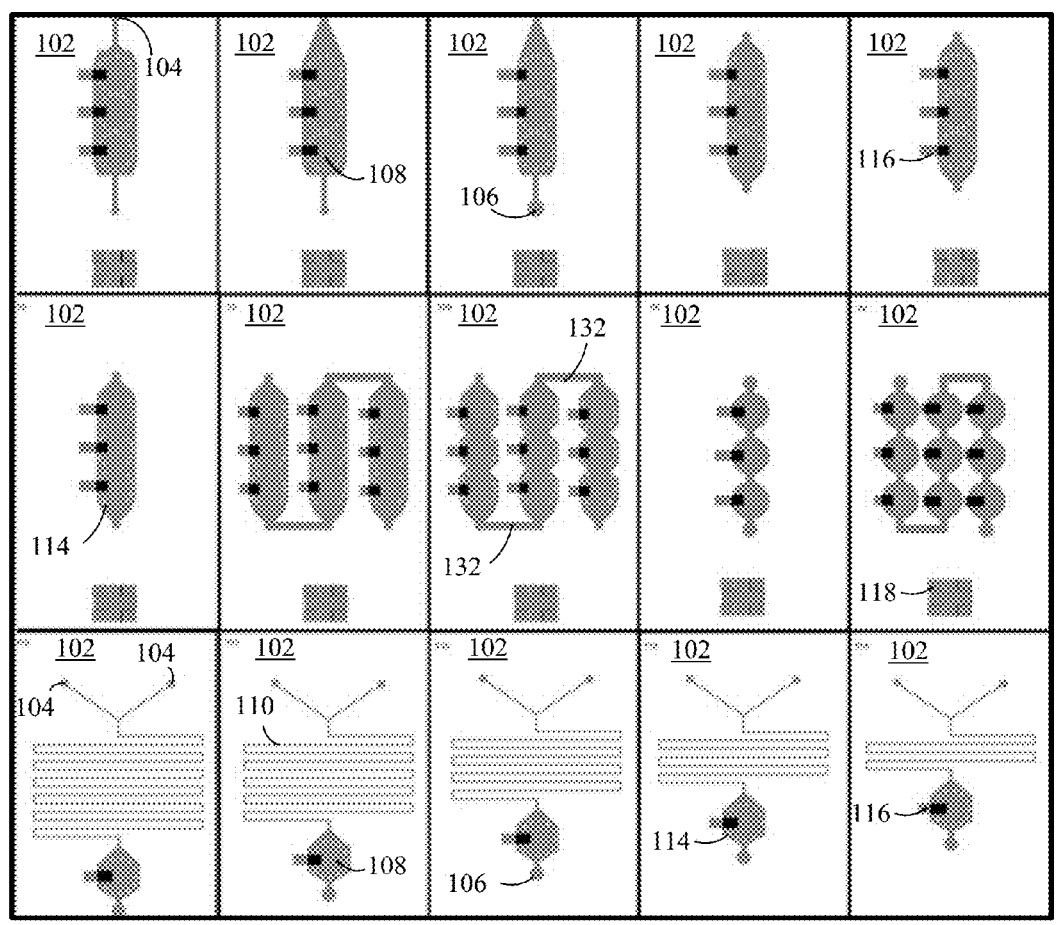
FIG. 9 provides several embodiments of a bottom platform having multiple grid chambers (top two rows) and fluidic timers (bottom row).

Referring now to FIG. 9, an embodiment may include multiple grid chambers in fluidic communication and arranged in series or in parallel to create microfluidic timers for fluid delivery/fluid interaction and/or to increase the production rate of EM samples. The first two rows of bottom platforms 102 provides various examples of how multiple fluidly coupled grid chambers might be arranged. The third row of bottom platforms 102 depicts exemplary embodiment of microfluidic timers used with a single grid chamber 108. As illustrated in the first two rows, each set of fluidly coupled grid chambers includes a single inlet 104 and a single outlet 106. The grid chambers 108 may be arranged in any configuration and may be coupled through various intermediate channels 132. Furthermore, each grid chamber 108 preferably includes a plurality of support barriers 114 for securing an EM grid within a particular grid chamber 108. Likewise, each grid chamber 108 preferably includes an extraction divot 116 for removing an EM grid from a particular grid chamber 108. These fluidly coupled grids significantly improve the speed at which samples can be prepared compared to the conventional manual preparation.

The third row of bottom platforms 102 depicts exemplary embodiments of microfluidic timers used with a single grid chamber. Two inlets 104 may be used to create timed reactions, which occur while the injected fluids pass through inlet channel 110 to grid chamber 108. By using different length inlet/mixing channels 110, the time for the sample to reach grid chambers 108 and for the reaction to occur can vary.

Figure 10:
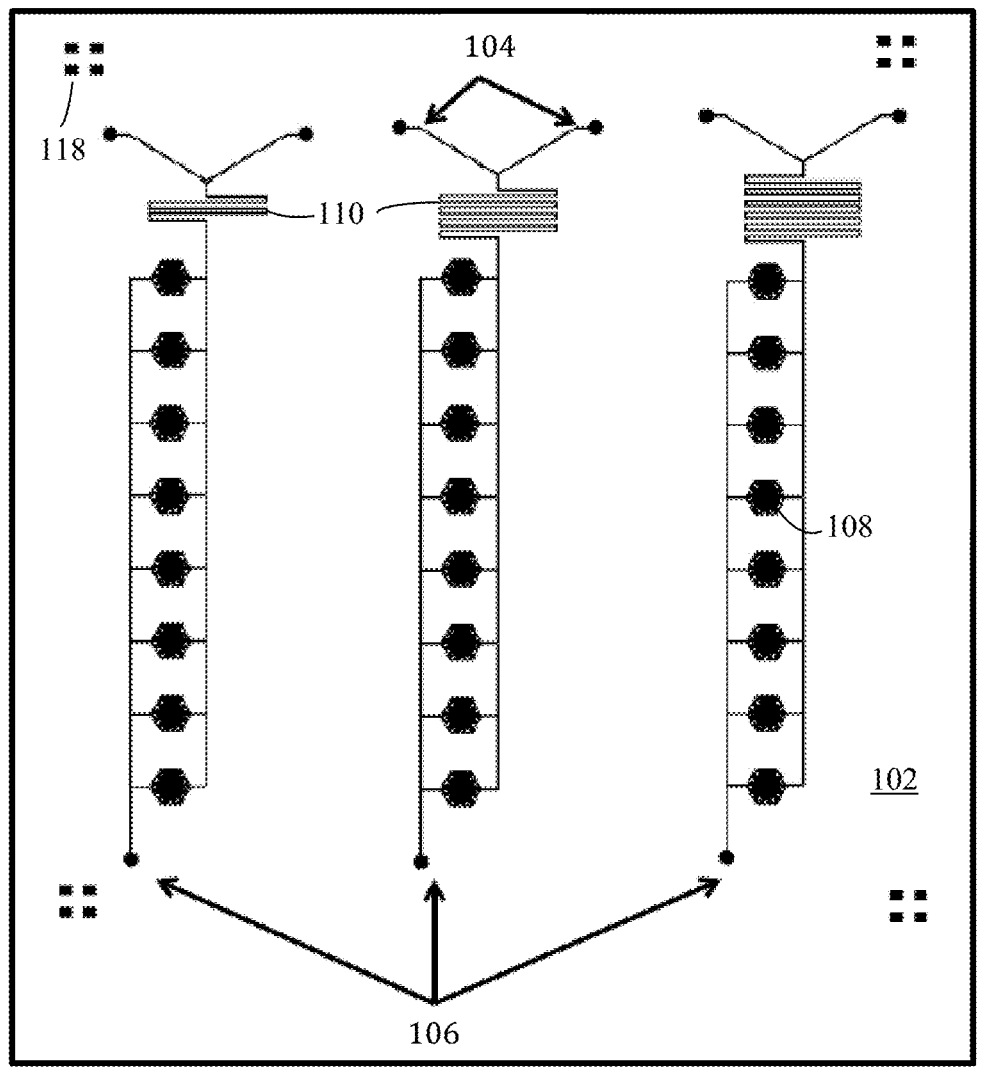
FIG. 10 is an exemplary embodiment of bottom platform illustrating the possibility of combining multiple sets of grid chambers with each set coupled to a microfluidic timer.

Referring to FIG. 10, an embodiment of platform 102 may include grid chambers 108 in series with each series coupled to a microfluidic timer comprising two inlets 104 converging to inlet channel 110. This arrangement produces different incubation and mixing times and allows for complexes and reactions to reach different states before entering each sequential grid chamber. The time points of reaction can be recorded in a "snap-shot" by sequentially applying the sample to the series of grids to capture time-dependent processes. Likewise, fixative could be delivered at specific time increments to trap complexes at different stages of activity.

Figure 11:
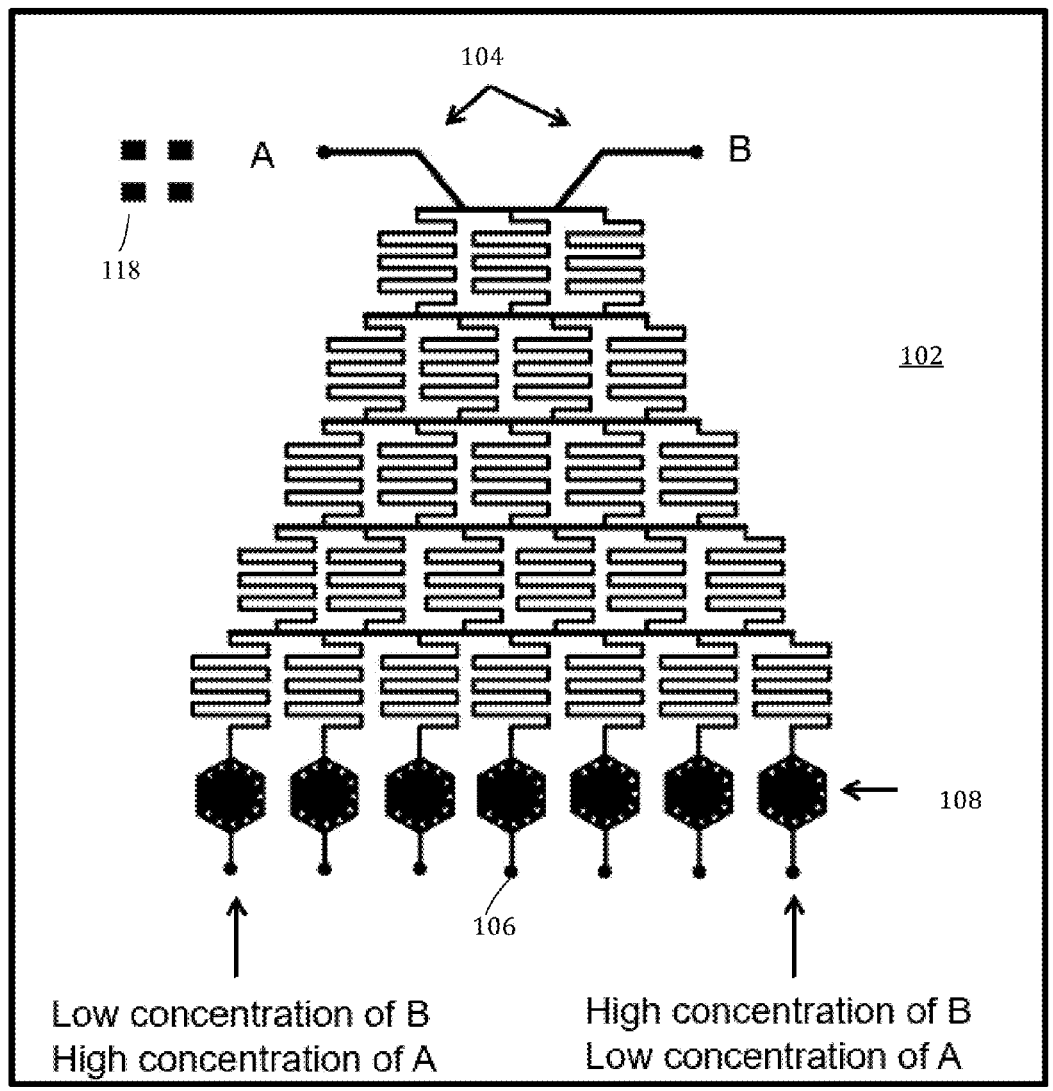
FIG. 11 is an exemplary embodiment of bottom platform illustrating the use of a gradient generator with multiple grid chambers.

An embodiment, as shown in FIG. 11, may employ a gradient generator to mix a panel of different conditions to study their effect on a structure of a complex/molecule. This can also be used to study time-dependent assembly mechanisms and reactions. A multitude of samples can be created by adjusting the variable parameters, which include, but are not limited to, the number of inputs and complex gradients, the mixing times and reaction times, the flow rates, and the amount of grids that can be screened.

The embodiment of bottom platform 102 provided in FIG. 11 includes a gradient between inlets 104 and grid chambers 108. As shown, fluid A is inserted into the left inlet and fluid B is inserted into the right inlet. The gradient creates varying concentrations of the two fluids in each grid chamber 108. The leftmost grid chamber has a low concentration of fluid B and a high concentration of fluid A. The reverse is true at the rightmost grid chamber and varying concentrations can be found in the grid chambers between the two outer grid chambers.

Figure 12:
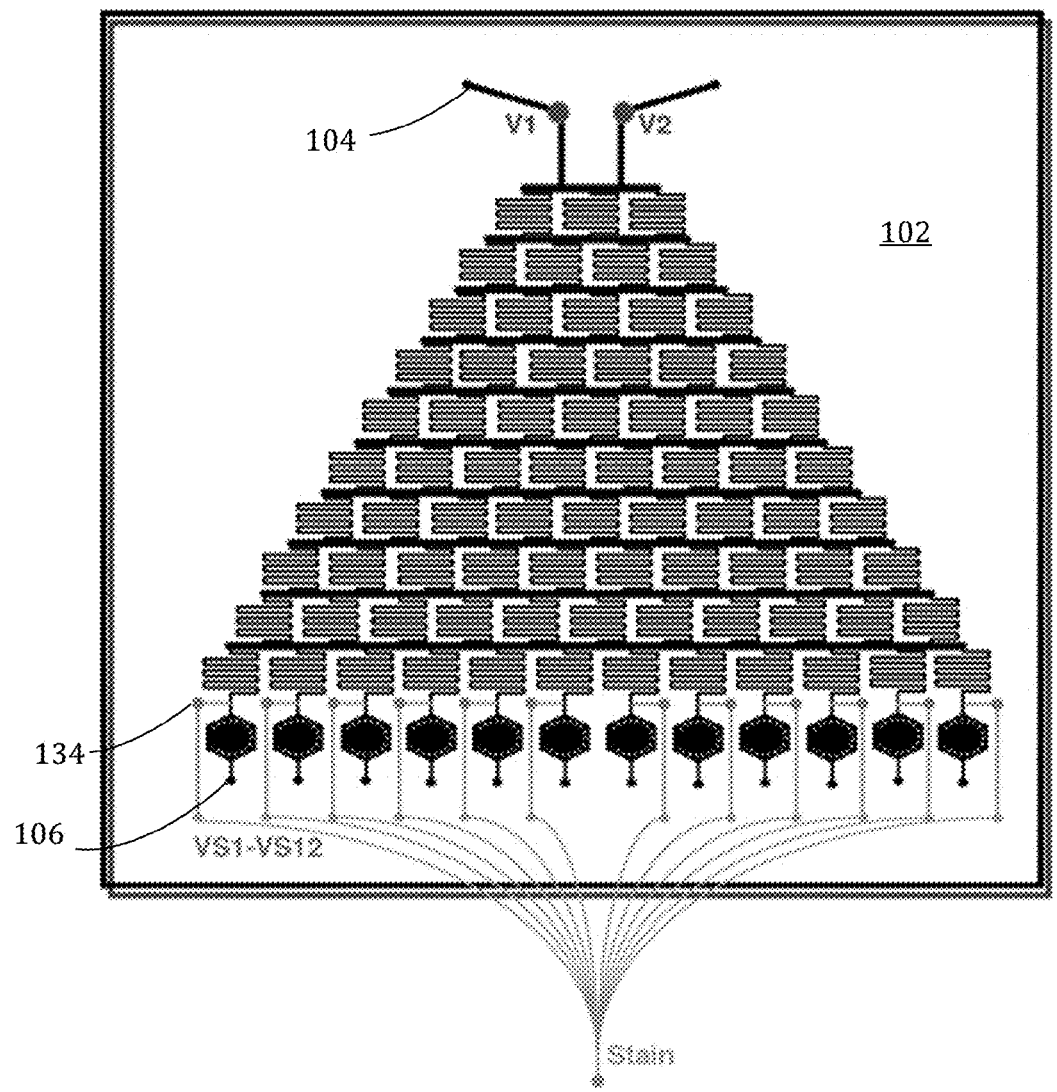
FIG. 12 is an exemplary embodiment of bottom platform illustrating the use of a gradient generator with multiple grid chambers and an additional sample inlet.

An embodiment shown in FIG. 12 includes an additional stain delivery inlet 134 to apply stain directly to the grid instead of flowing it through the gradient channels. The embodiment may also include soft lithography valving (V1, V2, VS1-VS12), which are used to shunt the flow only for the desired paths. This prevents backflow of stain for the sample delivery and allows the devices to be reused.

Figure 13:
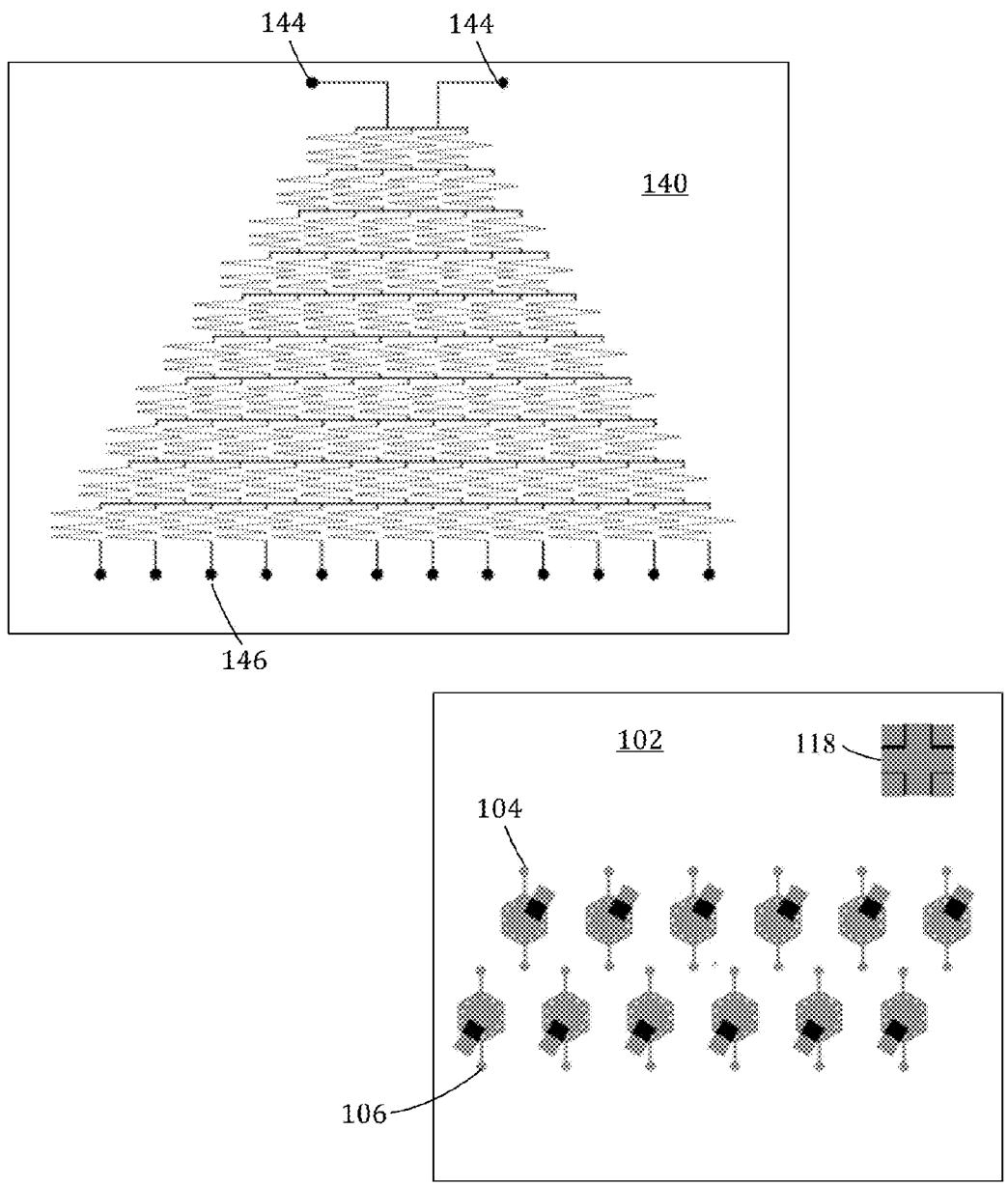
FIG. 13 depicts the use of an embodiment of a bottom platform with a separate gradient generator platform.

In an embodiment as shown in FIG. 13, bottom platform 102 may be separate from gradient platform 140. Fluids are first inserted into gradient inlets 144, and after mixture, the fluid exists gradient outlets 146. Outlets 146 are fluidly coupled (not depicted) to inlets 104 for each grid chamber 108 in bottom platform 102. A separate gradient platform allows for simplistic and efficient replication of use.

Experimental Research

The reagents used in the experiment included nitric acid, hydrogen peroxide, hydrofluoric acid, sodium hydroxide, ethanol, and (tridecafluoro-1,1,2,2-tetrahydrooctyl) trichlorosilane. Ultrapure deionized water was used for all solutions and sample preparation, and KvBeta was recombinantly expressed in and purified using known methods.

Fabrication.

Figure 14:
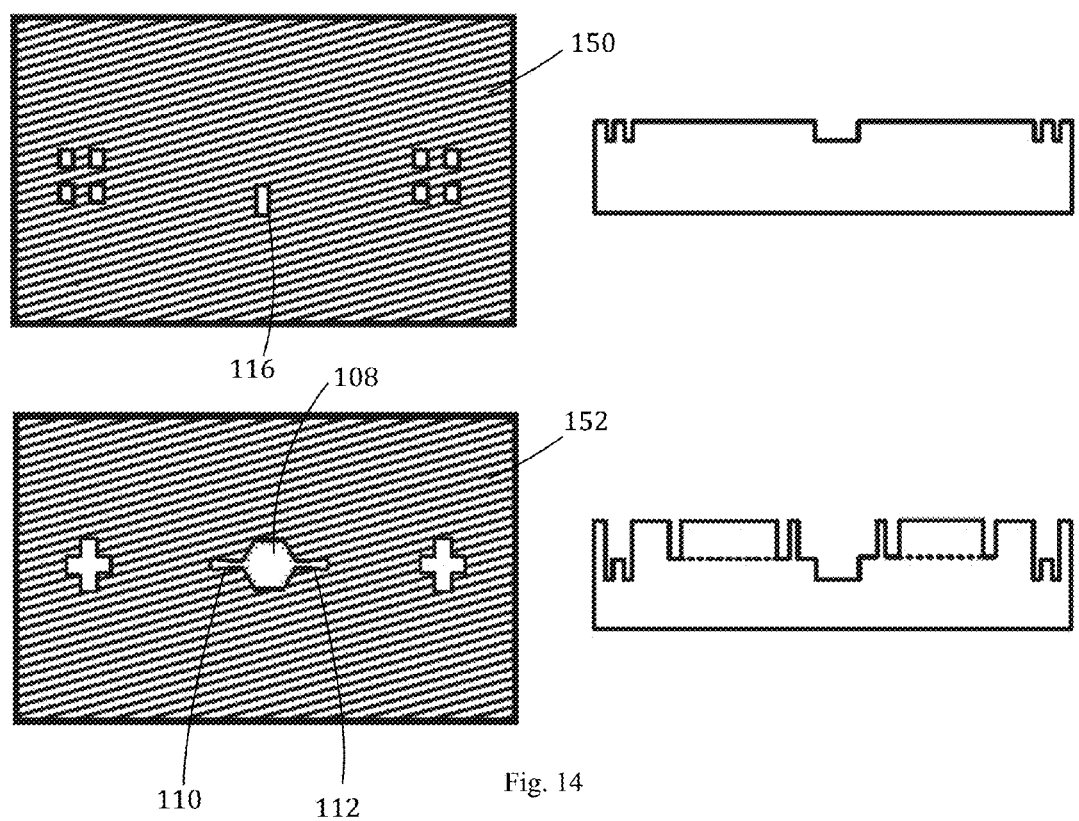
FIG. 14 depicts an exemplary method for manufacturing the platforms. The photomasks on the left half are used to fabricate the platforms shown on the right using photo lithography. In order to obtain two different depths, separate exposure and etching steps are implemented. First an extraction divot is etched into the glass and subsequently the grid chambers and channels are added. This may allow for the integration of plumbing and an extraction pathway.

In order to get multiple depth steps in a single platform, the microfabrication steps were repeated twice on the same wafer (FIG. 14). First, borofloat photoresist wafers with a layer of AZ1500 positive photoresist on a chrome layer were exposed to 18 mW $cm^{-1}$ collimated UV radiation for 15 seconds through mylar, patterned photomask 150 containing extraction divot 116. The exposed photoresist was removed with AZ 400K Developer, diluted 1:3 in H2O. The bottom chrome layer was then developed with a chrome etchant solution. The exposed glass was then etched in a 5:1:3 (v:v:v) mixture of H2O:HNO3:HF to a 40 µm depth. For the second step, the wafer was aligned with photomask 152 containing the design with the channels 110, 112 and grid chamber 108. The features were developed and etched again to a depth of 110 µm. This produced a channel depth of 70 µm with an extraction divot of 40 µm. The total chamber volume was 3 µL.

The same process was repeated for another chip, developing the mirror reflection of the design features, this would serve as the top complement platform. All dimensions of the channels were verified using a P-15 stylus profilometer. Fluid access holes were drilled with a 1.1 mm diamond-tipped drill bit, after which the remaining photoresist and chrome were removed. The finished top platform was then fitted with a nanoport that was attached using epoxy.

For the surface modification, the glass was cleaned by submerging in 5 M NaOH for 10 minutes. The surface was rinsed with water and dried with $N_2$. Subsequently the platforms were oxidized in a plasma cleaner for 2 minutes. Immediately after, the platforms were placed in a vacuum desiccator and (tridecafluoro-1,1,2,2-tetrahydrooctyl) trichlorosilane was deposited using a known method. Subsequently, the platforms were rinsed with water, dried with $N_2$, and stored in clean petri dishes at room temperature until use.

Sample Preparation.

The bottom glass platform was placed into the aluminum manifold. A carbon coated, copper grid was rendered hydrophilic using a plasma cleaner and gently placed into the device chamber. Several 20 µL drops of buffer (20 mM Tris pH 8.0, 150 mM KCl, 1 mM 2-mercaptoethanol) were distributed around the non-etched parts of the glass platforms. The top platform was aligned using the manifold and lowered on top of the bottom platform, in process displacing the buffer and creating a thin sealing layer. The top of the manifold was attached and screwed down to seal the device. 20 µL of sample was loaded in the inlet and a vacuum was applied at the outlet to fill the chamber with sample. Alternatively, the sample could be delivered to the inlet using a syringe with appropriate fitting. The vacuum was removed and the sample was left in the chamber for 10 seconds after which 50 µL of uranium acetate stain was loaded into the inlet and carried through with vacuum. After 10 seconds, compressed air was blown into the inlet and used to dry the grid. The air also purged the thin film of buffer between the platforms, enabling the device to be opened and the grid extracted via the divot with a pair of forceps.

Electron Microscopy and Reconstruction.

EM micrographs of Kvβ2.1 were collected on a CM-120 BioTwin operating at 120 keV at room temperature with a nominal pixel size of 2.88 angstroms per pixel equipped with a Tem-Cam F224 slow scan CCD camera. EM micrographs were uploaded to the Appion processing suite. Kvβ2.1 particles were picked in a semi-automatic fashion using the template picker FindEM. Two dimensional (2D) class averages were generated using the maximum likelihood alignment algorithm within the Xmipp package.

Results and Discussion.

Reproducibility in the staining process was attained by integrating all the sample preparation steps into a single device that housed the EM grid (FIG. 4). Further advantages realized through various embodiments include, but are not limited to: (1) simplicity of use and no requirement for further accessories, (2) easily fabricated and reusable and (3) the system is amenable for integration of further "on-chip" valving and plumbing.

After grid 120 was placed in the chamber, it was confined by support barriers 114 to prevent sliding and flow induced friction that could tear the carbon film containing the sample. In absence of support barriers, EM grid 120 became torn upon application of the sample. The support barriers preserved the grid integrity completely. Extraction divot 116 also permitted easy grid access and extraction. Upon disassembling of the device, grid 120 would occasionally stick to top platform 122. To address this problem, a divot 116 and set of barriers 114 were etched into top platform 122 as well, permitting extraction without sticking.

In order to interface microfluidics with EM preparation, reversible sealing of the grid inside a device is required. This was achieved by silanizing the glass surface with (tridecafluoro-1,1,2,2-tetrahydrooctyl) trichlorosilane, producing an eight carbon long, fluorinated moieties on the surface. This rendered the glass both fluorophilic and hydrophobic. The fluorophilic surfaces of the two glass platforms interact with each other and form a non-covalent interaction, sufficient to seal the chip reservoir and channels. The fluorophilic surfaces may prevent the sample from wicking in between the platforms, yet the force is sufficient to incorporate syringe pump integration. The platforms appeared to seal better when a film of buffer was introduced between the platforms. This is believed to be due to an alignment of the fluorinated chains that might be in a collapsed state when dehydrated. In some embodiments, longer alkane chains with higher amount of fluorination may be used to strengthen the glass bond while maintaining reversible sealing.

Besides the improvement in the reproducibility of the staining, the cleanliness of the grids was improved and found to be free of particulate contamination. When making grids, contamination known as "crud" is the norm yet it consumes functional space on the grid and has the potential to interfere with the sample application and staining. By incorporating all the steps into a single device as shown in FIG. 4, contamination was effectively eliminated.

Figure 15:
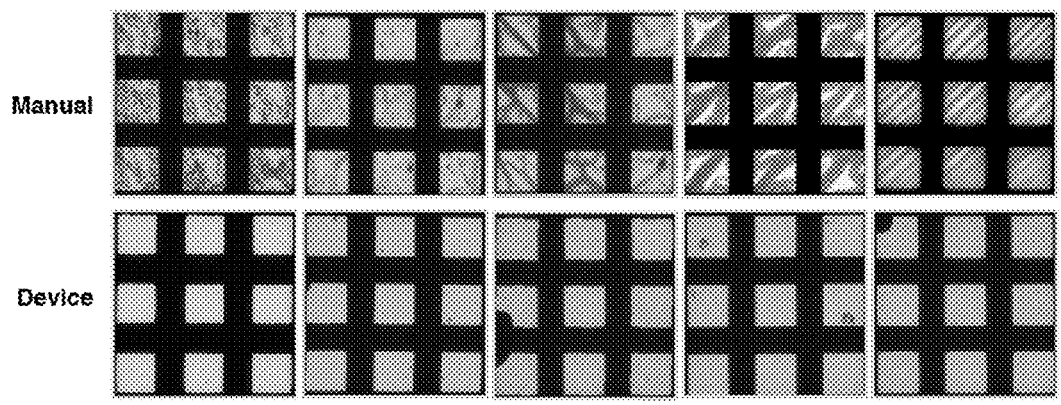
FIG. 15 illustrates low magnification (130×) images of artifacts resulting from conventional manual preparation (top row) and from preparation according to the present invention (bottom row).

The contamination of the grids was compared between the hand prepared grids and the grids prepared using the device of the present invention, which is depicted in FIG. 15. All images were taken from separately prepared grids, however, the grids were prepared using the same sample and on the same day. The second row of images corresponds to the grids prepared using the present invention. As is shown, the grids are predominantly clean, only infrequent particulates are observed, and the stain thickness is even throughout the grid. The top row of images corresponds to grids prepared by hand under the prior art methodology. When prepared by hand, abundant contamination with particulates and debris are evident. In addition, vast differences between hand prepared grids, including striations of different stain thicknesses produced during the drying process, illustrate the variability in the staining process. In contrast, the grids, produced using the device of the present disclosure, were reproducibly prepared, with similar stain thickness and in absence of contamination. Clearly the present invention aids in sample preparation and will help transition this technology to non-expert users.

Figure 16:
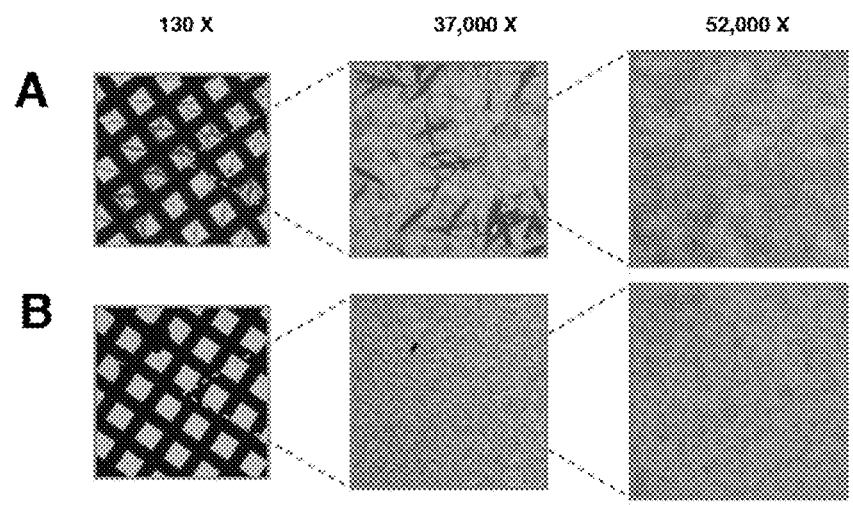
FIG. 16 provides a comparison between the samples prepared by hand (row A) and the samples prepared by the present invention (row B) by way of high magnification images.

The collective quality of the images acquired following preparation in the device of the present invention was equal if not better to those prepared by hand. A magnification series comparing both preparations is shown in FIG. 16. The sample contamination is evident in the low magnification image prepared by hand (first image in row A). Nonetheless, stained KvBeta particles can be discerned at the higher magnifications. When using the device of the present invention, depicted in row B, the particles appear to be more evenly distributed with a denser stain. As the magnification increases, the Kvβ2.1 particles are seen as monodisperse and evenly stained yielding strong signal to noise. The cleaner surfaces provided with the device may increase the available area for imaging, minimize variability, and increase reproducibility of the staining methods. The final stain images at 52 k magnification are comparable, with slightly improved stain coverage when using the device.

Figure 17:
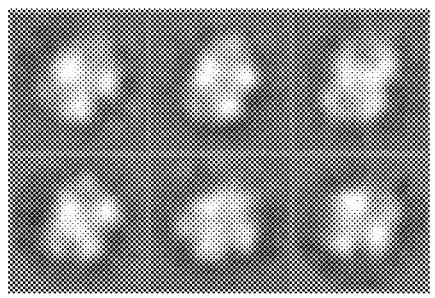
FIG. 17 illustrates two-dimensional reference free class average of Kvβ2.1 particles picked from micrographs prepared using the sample preparation device of the present disclosure.

To illustrate the viability of this approach for structural biology, a 2D class average of the Kvβ2.1 complex was performed (FIG. 17). The reconstruction reveals structural motifs comparable to methods performed by hand and validates the coupling of microfluidics with EM sample preparation.

Glossary of Claim Terms

Fluid Delivery Mechanism: is a device configured to transfer fluid from one location to another location.

Gradient Generator: is a plurality of fluidic channels designed to increase or decrease the concentration of a fluid observed in passing from one gradient outlet to another gradient outlet.

Microfluidic Timer Channel: is a fluidic channel having an indirect extended route between an inlet and the grid chamber.

Platform: is a generally rigid material, such as glass.

Stain: is a fluid used to artificially highlight tissue, microorganisms, and other biological structures for viewing, typically under a microscope.

REFERENCES

Castro-Hartmann P, Heck G, Eltit J M, et al. The ArrayGrid: A methodology for applying multiple samples to a single TEM specimen grid. *Ultramicroscopy* 2013; 135: 105-112.

Giss D, Kemmerling S, Dandey V, et al. Exploring the interactome: microfluidic isolation of proteins and interacting partners for quantitative analysis by electron microscopy. *Anal. Chem.* 2014; 86: 4680-4687.

Jain, Tilak, et al. Spotiton: A prototype for an integrated inkjet dispense and vitrification system for cryo-TEM. *J. Struct. Biol.* 2013; 179: 68-75.

Kemerling S, Arnold S A, Bircher B A, et al. Single-cell lysis for visual analysis by electron microscopy. *J. Struct. Biol.* 2013; 183: 467-473.

Kemmerling S, Ziegler J, Scheighause G, et al. Connecting u-fluidics to electron microscopy. *J. Struct. Biol.* 2012; 177: 128-134.

Lu, Zonghuan, et al. Gas-assisted annular microsprayer for sample preparation for time-resolved cryo-electron microscopy. *J. Micromech. Microeng.* 2014; 24:115001.

Lu, Zonghuan, et al. Monolithic microfluidic mixing—spraying devices for time-resolved cryo-electron microscopy. *J. Struct. Biol.* 2013; 168: 388-395.

Where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A microscope grid preparation device, comprising:
    a bottom platform having upper and lower surfaces, the bottom platform further including:
        a grid chamber extending downwardly from the upper surface;
        a plurality of support barriers disposed within the grid chamber and extending upwards from a base of the grid chamber towards the upper surface of the bottom platform, the plurality of support barriers arranged in a shape conducive for securing a microscope grid within the grid chamber;
        an extraction divot having at least a portion of the divot located within the grid chamber, a bottom surface residing at a depth in the bottom platform that is greater than a depth of the grid chamber, and a width less than a width of the grid chamber, thereby enabling a portion of an extraction tool to pass under the grid chamber for easy removal of a microscope grid within the grid chamber;
        an inlet in fluid communication with the grid chamber;
        an outlet in fluid communication with the grid chamber;
    a top platform having upper and lower surfaces, wherein the lower surface is configured to rest in overlying relation to the bottom platform, the top platform further including:
        an inlet aperture creating a through hole between the upper surface and lower surface of the bottom platform, thereby allowing fluid to pass from the upper surface of the top platform into the inlet in the bottom platform; and
        an outlet aperture creating a through hole between the upper surface and lower surface of the bottom platform, thereby allowing fluid to pass from the outlet in the bottom platform to the outlet aperture in the top platform.

2. The device of claim 1, wherein the top and bottom platforms are configured to become temporarily secured together to seal off the grid chamber from the environment.

3. The device of claim 1, wherein the inlet and outlet apertures in the top platform are coupled to a fluid delivery mechanism.

4. The device of claim 1, wherein the top platform includes an alignment marker on the lower surface, the bottom platform includes an alignment marker on the upper surface, and the alignment markers are designed to interact with each other when the upper surface of the bottom platform and the lower surface of the top platform are forced together.

5. The device of claim 1, wherein the top platform further includes:
- a grid chamber extending upwardly from the lower surface;
- a plurality of support barriers disposed within the grid chamber and extending downwards from a base of the grid chamber towards the lower surface of the top platform, the plurality of support barriers arranged in a shape conducive for securing the microscope grid within the grid chamber; and
- an extraction divot having at least a portion of the divot located within the grid chamber, a top surface located closer towards the upper surface of the bottom platform than the base of the grid chamber, and a width less than a width of the grid chamber, thereby enabling a portion of the extraction tool to pass above the grid chamber for easy removal of the microscope grid within the grid chamber.

6. The device of claim 1, further including a top platform having the same features as the bottom platform, wherein the top platform is inversely secured to the bottom platform in a sealed fashion, such that the top surface of the top platform is in covering relation to the top surface of the bottom platform.

7. The device of claim 1, further comprising the bottom platform having:
- a second grid chamber extending downwardly from the upper surface;
- a second plurality of support barriers disposed within the second grid chamber, wherein each support barrier extends upwards from a base of the second grid chamber towards the upper surface of the bottom platform and the second plurality of support barriers are arranged in a shape conducive for securing a microscope grid within the second grid chamber;
- a second extraction divot having at least a portion of the second divot located within the second grid chamber, a bottom surface residing at a depth in the bottom platform that is greater than a depth of the second grid chamber, and a width less than a width of the second grid chamber, thereby enabling a portion of an extraction tool to pass under the second grid chamber for easy removal of the microscope grid disposed within the grid chamber;
- an inlet channel in fluid communication with the second grid chamber; and
- an outlet channel in fluid communication with the second grid chamber.

8. The device of claim 7, further comprising a gradient generator disposed within the top surface of the bottom platform, the gradient generator having two or more gradient inlets for receiving fluids and two or more gradient outlets with each gradient outlet in fluid communication with one inlet.

9. The device of claim 1, wherein the support barriers are arranged in a semi-circular formation.

10. The device of claim 1, wherein the bottom plate further includes a second inlet in fluid communication with the grid chamber and the inlet through a microfluidic timer channel.

11. A method for preparing microscope samples, comprising:
- inserting a microscope grid within a support barrier perimeter established by plurality of support barriers disposed within a grid chamber in a bottom platform;
- temporarily securing a top platform overtop the bottom platform;
- delivering a first fluid into an inlet aperture, wherein the inlet aperture is in fluid communication with grid chamber;
- propelling the first fluid through the grid chamber and out through an outlet aperture in fluid communication with the grid chamber;
- delivering a second fluid into the inlet aperture and propelling the second fluid through the grid chamber and out through the outlet aperture; and
- drying the microscope grid through insertion of a gas into the inlet.

12. The method of claim 11, further comprising the steps of removing the top platform and removing the microscope grid from the grid chamber.

13. The method of claim 12, wherein the step of removing the microscope grid includes inserting a distal end of an extraction tool into an extraction divot to aid in grasping the microscope grid, wherein the extraction divot extends deeper into the bottom platform than the grid chamber and includes at least a portion disposed within the grid perimeter.

14. The method of claim 11, wherein the first fluid includes a sample of interest.

15. The method of claim 11, wherein the second fluid is a stain.

16. The method of claim 11, further comprising the step of aligning a grid chamber in the top platform with the grid chamber in the bottom platform before temporarily securing the top platform to the bottom platform.

17. The method of claim 11, wherein the step of temporarily securing a top platform overtop the bottom platform includes temporarily sealing the top platform and bottom platform together.

* * * * *